United States Patent [19]

Nakamura

[11] Patent Number: 5,528,417
[45] Date of Patent: Jun. 18, 1996

[54] STAND APPARATUS FOR MEDICAL OPTICAL EQUIPMENT

[75] Inventor: Katsushige Nakamura, Tokyo, Japan

[73] Assignee: Mitaka Kohki Co., Ltd., Tokyo, Japan

[21] Appl. No.: 290,767

[22] PCT Filed: Dec. 28, 1994

[86] PCT No.: PCT/JP93/01923

§ 371 Date: Aug. 17, 1994

§ 102(e) Date: Aug. 17, 1994

[87] PCT Pub. No.: WO94/14387

PCT Pub. Date: Jul. 7, 1994

[30] Foreign Application Priority Data

Dec. 28, 1992 [JP] Japan ................. 4-358629

[51] Int. Cl.$^6$ ................................. G02B 21/00
[52] U.S. Cl. ................................. 359/384; 359/368
[58] Field of Search ................ 359/384, 382, 359/368; 248/123.1, 280.1, 542

[56] References Cited

U.S. PATENT DOCUMENTS

| 3,887,267 | 6/1975 | Heller .................. 359/384 |
| 4,339,100 | 7/1982 | Heller et al. ............ 359/368 |
| 4,684,088 | 8/1987 | Heller .................. 248/123.1 |
| 4,881,709 | 11/1989 | Nakamura .............. 248/123.1 |
| 5,173,802 | 12/1992 | Heller .................. 359/384 |
| 5,186,422 | 2/1993 | Nakamura .............. 359/382 |
| 5,205,522 | 4/1993 | Nakamura .............. 359/384 |

FOREIGN PATENT DOCUMENTS

| 0237968 | 9/1987 | European Pat. Off. . |
| 0552524 | 7/1993 | European Pat. Off. . |
| 2311257 | 9/1974 | Germany . |
| 56-32110 | 4/1981 | Japan . |
| 156409 | 3/1989 | Japan . |
| 2-71514 | 5/1990 | Japan . |

OTHER PUBLICATIONS

Abstract of Japanese Laid Open Patent No. 1–56409.

*Primary Examiner*—Paul M. Dzierzynski
*Assistant Examiner*—Steve Kong
*Attorney, Agent, or Firm*—Michael D. Bednarek; Marks & Murase

[57] ABSTRACT

A crank member 34 is supported to a joint shaft $\beta_1$, and a horizontal fulcrum $\beta_6$ on the crank member 34 and a portion $\beta_8$ of a stand 18 are connected together by a vertical sublink 37, whereas a vertical fulcrum $\beta_7$ on the crank member 34 and a portion $\beta_9$ of a front link 27 are connected together by a horizontal sublink 38. Accordingly, the front link 27 supporting a medical optical equipment 33 is always kept in a substantially vertical condition. As a result, there is no danger that the front link 27 may largely swing to strike against any persons in the periphery thereof, thus providing a stand apparatus desirable from the viewpoints of operability and sanitariness.

6 Claims, 9 Drawing Sheets

STAND APPARATUS FOR MEDICAL OPTICAL EQUIPMENT

TECHNICAL FIELD

This invention relates to a stand apparatus for use in microsurgery, capable of supporting an operating microscope and its associated equipment, which are heavy objects, with use of a supporting linkage mechanism utilizing a parallel linkage and balancing the weight of these elements with use of a counterweight to thereby keep the operating microscope and the like still in the air.

BACKGROUND ART

A surgical operation such as a brain surgical operation and heart surgical operation is performed with an affected part being observed by an operator through an operating microscope. Accordingly, the operator strains his/her nerve because of very minute operation, and in many cases much time is spent for the operation. Such a long operating time will undesirably cause an increase in physical and mental fatigues of both the subject and the operator.

A medical optical equipment such as an operating microscope plays a very important role in such a high-level operation, and easiness of use of the medical optical equipment directly follows a reduction in the operating time. A conventional stand apparatus for permitting the medical optical equipment to be easily used is shown in FIGS. 10 and 11, for example (see Japanese Patent Laid-open No. Sho 56-32110 and corresponding U.S. Pat. No. 4,339,100).

Referring to FIG. 10, reference numerals 1 and 2 denote a base and a stand, respectively. The stand 2 is rotatable about a vertical axis α of rotation relative to the base 1. An electromagnetic clutch C is provided between the stand 2 and the base 1 to lock a rotational position of the stand 2 relative to the base 1. The base 1 is provided on its lower surface with casters 3 each having a locking mechanism and a vertically moving mechanism, thereby permitting the base 1 to be moved on an upper surface of a floor F and further permitting the base 1 to be locked at a desired position and to be adjusted in levelness.

A first parallel linkage 4 is pivotally mounted through a fulcrum 5 to an upper end portion of the stand 2. The first parallel linkage 4 is rotatable about the fulcrum 5 in a frontward direction (a direction shown by an arrow A) or in a rearward direction (a direction shown by an arrow B), and can be locked by an electromagnetic clutch (not shown) provided at the fulcrum 5. An upper end of the first parallel linkage 4 is formed by a horizontal shaft 6, and a second parallel linkage 7 and a third parallel linkage 8 are interlockingly mounted to the horizontal shaft 6. A front end of the third parallel linkage 8 is formed by a front link 9 extended downwardly, and an operating microscope 10 is mounted to a lower end of the front link 9.

The operating microscope 10 is located below an extension L of the horizontal shaft 6. Accordingly, the operating microscope 10 itself functions as a kind of weight to form a balancing structure like a so-called "yajirobei (balancing toy)", and the operating microscope 10 is swingable about an intersection 11 between the extension L and the front link 9, so that an operator can arbitrarily change an observation angle of the operating microscope 10 to observe an opened portion of the head of a subject 12. Further, electromagnetic clutches (not shown) provided at joint shafts 13 for joining the parallel linkage 7 to the horizontal shaft 6, thereby locking the swing position of the operating microscope 10 after changing the observation angle.

In such a conventional stand apparatus for a medical optical equipment, however, the front link 9 is swung about the intersection 11 in concert with the change in the observation angle of the operating microscope 10 by the operator 14 as shown in FIG. 11. Accordingly, there is a possibility that the front link 9 may strike against an assistant 15 present near the operator 14. Further, depending upon the observation angle, the front link 9 may strike against the operator 14 himself/herself. Thus, the operability of the stand apparatus is bad. Further, as the front link 9 itself has not been perfectly sterilized, the touch of the front link 9 with the operator 14 or the like is undesirable from a sanitary view. Further, the location of the stand apparatus of this kind is selected to an optimum position according to the content of the operation to be performed. That is, while a specific position in the periphery of the subject 12 is selected by indication from the operator 14, the work of moving the stand apparatus to the specific position and setting it at this position is carried out by a person not taking part in the operation because of sanitary demand. After moving the stand apparatus to the indicated position and then locking it, this person must carry out horizontal adjustment of the stand apparatus to make it perfectly horizontal. That is, since the floor F of an operating room is not perfectly horizontal, such horizontal adjustment is required. If the horizontal adjustment is not carried out, the vertical axis α becomes inclined. As a result, at the instance the electromagnetic clutch C is disengaged, the stand 2 and the structure thereabove possibly start largely rotating about the vertical axis α. In this manner, every time the position of the stand apparatus in the prior art is changed, the horizontal adjustment must be carried out at the position after changed. Thus, the stand apparatus in the prior art is very troublesome to handle.

This invention has been achieved in view of the problems mentioned above, and it is an object of the present invention to provide a stand apparatus for a medical optical equipment which can prevent a link member supporting the medical optical equipment from largely swinging during operation of the equipment and eliminate the need of the horizontal adjustment.

DISCLOSURE OF INVENTION

According to an aspect of the present invention, there is provided a stand apparatus for a medical optical equipment characterized in that:

a pair of parallel vertical links and a pair of parallel horizontal links are combined to form a parallel linkage, and an intermediate portion of one of the vertical links is pivotally supported through a fulcrum to a stand disposed on a floor;

an upper one of the horizontal links of the parallel linkage is extended to form a supporting link, and a substantially vertical front link is pivotally supported to the supporting link at a front end thereof, the medical optical equipment being supported to a lower end of the front link;

a joint shaft or the parallel linkage is set at a rear end of the supporting link, and a crank member having a horizontal fulcrum lying on a horizontal line on which the joint shaft lies and a vertical fulcrum lying on a vertical line on which the joint shaft lies is supported to the joint shaft, the horizontal fulcrum of the crank member and a portion of the stand being connected together by a vertical sublink parallel to the one vertical link of the parallel linkage and having a length equal to that between the joint shaft of the one vertical link and the fulcrum of the parallel linkage, the vertical fulcrum of the crank member and a portion of the front link being connected together by a horizontal sublink parallel to the supporting link and having a length equal to that of the supporting link; and a counterweight is provided below the parallel linkage to counterbalance a weight applied in a lowering direction of the parallel linkage about the fulcrum and thereby keep the medical optical equipment still in a floating in the air.

Accordingly, even when the parallel linkage is deformed to move the medical optical equipment in the vertical direction and/or the horizontal direction, the front link supporting the medical optical equipment is kept always in a substantially vertical condition. Thus, there is no possibility that the front link may largely swing to strike against any persons in the periphery thereof, so that the stand apparatus is desirable from the viewpoints of operability and sanitariness.

According to another aspect of the present invention, a supporting parallel linkage unit having vertical links is provided at a lower end of the front link, and the medical optical equipment is supported to a lowermost horizontal link of the supporting parallel linkage unit.

With this structure that the medical optical equipment is mounted through the supporting parallel linkage unit to the lower end of the front link, the direction of the medical optical equipment can be changed even in the substantially vertical condition of the front link by deforming the supporting parallel linkage unit.

According to still another aspect of the present invention, the stand is rotatably mounted on a base disposed on the floor so as to be rotatable about a substantially vertical axis of rotation, and a weight of the stand and a structure thereabove is balanced with respect to the substantially vertical axis in each of at least two perpendicular directions.

With this structure that the weight of the stand and the structure thereabove is balanced with respect to the vertical axis in each of at least two perpendicular directions, there is no possibility that the stand and the structure thereabove may spontaneously rotate even when the stand is disposed on an inclined floor. Accordingly, it is unnecessary to carry out horizontal adjustment of the stand apparatus after moving it from one place to another, thereby greatly simplifying the handling of the stand apparatus.

According to still another aspect of the present invention, the intermediate portion of the one vertical link of the parallel linkage is pivotally supported through the fulcrum to the stand disposed on a wall of a room. As the stand is disposed on the wall of the room, a floor space can be widely utilized.

According to still another aspect of the present invention, the intermediate portion of the one vertical link of the parallel linkage is pivotally supported through the fulcrum to the stand disposed on a ceiling; a lower end of the horizontal links of the parallel linkage is extended to form the supporting link; and the counterweight is provided above the parallel linkage. Also in this structure, a floor space can be widely utilized as similar to the wall disposition type mentioned above.

It is to be noted that the parallelism to the vertical link or the horizontal link in the description mentioned above and below means the parallelism to a phantom straight line of the vertical link or the horizontal link. For example, when the vertical link or the horizontal link is partially curved, the parallelism to the vertical link or the horizontal link means the parallelism to a straight line connecting opposite ends of each link (or a straight line connecting one end of each link to the fulcrum). Accordingly, the length of the vertical link or the horizontal link means the length of such a straight line.

BEST MODE FOR CARRYING OUT THE INVENTION

Figure 1:
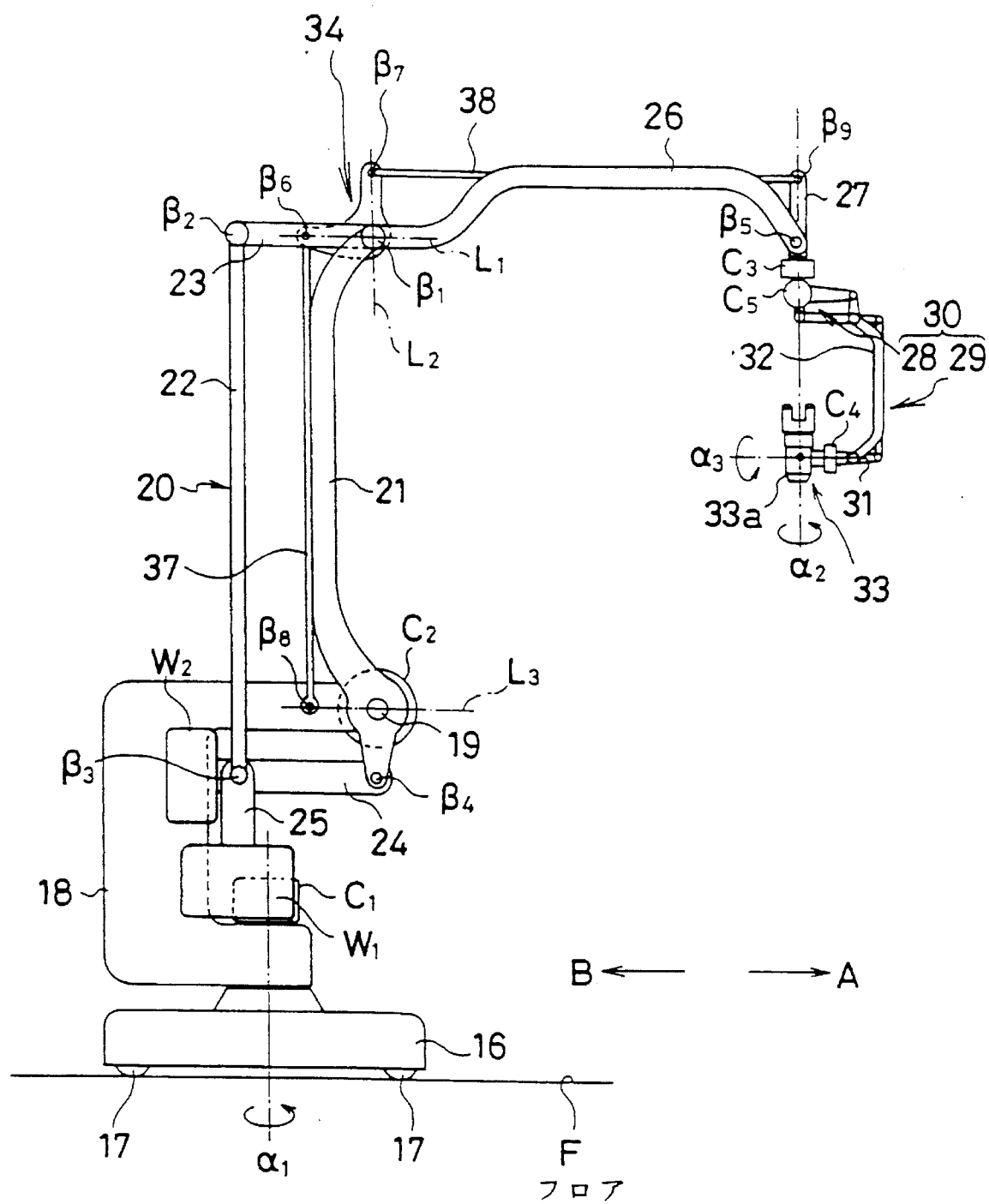
FIG. 1 is a side view of a stand apparatus for a medical optical equipment according to a first preferred embodiment of the present invention.

There will now be described some preferred embodiments of the present invention with reference to the drawings.

FIGS. 1 to 8 show a first preferred embodiment of the present invention. Reference numeral 16 denotes a base. The base 16 is provided on its lower surface with casters 17 each having a locking mechanism. The casters 17 allow the base 16 to be moved on a floor F. A stand 18 substantially U-shaped in side elevation is mounted on the base 16. The stand 18 is rotatable about a vertical axis $\alpha_1$ of rotation. An electromagnetic clutch $C_1$ is provided on the vertical axis $\alpha_1$ to stop rotation of the stand 18 and lock a rotational position of the stand 18.

A fulcrum 19 is set at a front end of an upper portion of the stand 18, and a parallel linkage 20 is supported to the fulcrum 19. The parallel linkage 20 is composed of a pair of parallel vertical links 21 and 22 and a pair of parallel horizontal links 23 and 24. These links 21 to 24 are pivotally joined together at their opposite ends by four joint shafts $\beta_1$ to $\beta_4$. A lower intermediate portion of the front vertical link 21 of the parallel linkage 20 is pivotally supported to the fulcrum 19. An electromagnetic clutch $C_2$ is provided on the fulcrum 19 to lock a pivotal position of the vertical link 21 (i.e., a deformed condition of the parallel linkage 20). The front vertical link 21 supported to the fulcrum 19 is curved rearward to have such a structure as not to interfere with an operator. A lever 25 is fixed to a lower end of the rear vertical link 22 so as to interlock integrally therewith, and a first counterweight $W_1$ is mounted on a lower end of the lever 25. Further, a second counterweight $W_2$ is mounted on a rear end of the lower horizontal link 24.

A supporting link 26 extends frontward from a front end of the upper horizontal link 23 of the parallel linkage 20 in an integral manner, and a vertical front link 27 is pivotally mounted through a joint shaft $\beta_5$ to a front end of the supporting link 26. The supporting link 26 is curved upward to have such a structure as not to interfere with the head of the operator.

Figure 5:
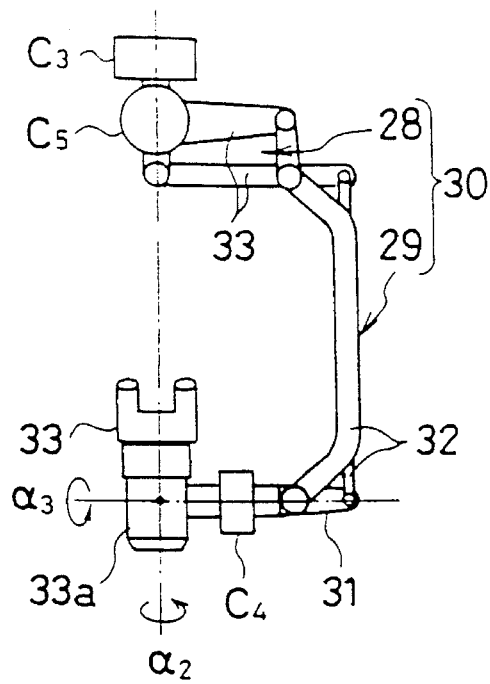
FIG. 5 is an enlarged side view of a supporting parallel linkage unit.
Figure 6:
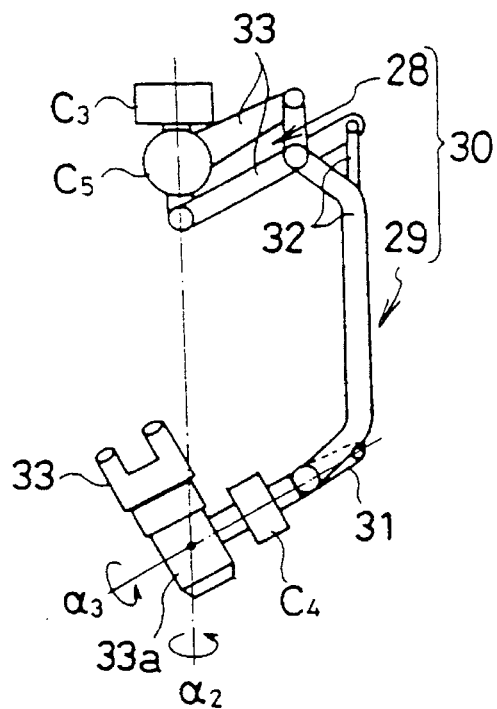
FIG. 6 is an enlarged side view similar to FIG. 5, showing a condition where the supporting parallel linkage unit is deformed.

As also shown in FIGS. 5 and 6, a supporting parallel linkage unit 30 consisting of two parallel linkages 28 and 29 interlocking each other is provided below the front link 27 so as to be rotatable about a vertical axis a $\alpha_2$ of rotation. An electromagnetic clutch $C_3$ is provided on the vertical axis $\alpha_2$ at an upper or base end of the supporting parallel linkage unit 30 to lock rotation of the supporting parallel linkage unit 30 about the vertical axis $\alpha_2$. An operating microscope (medical optical equipment) 33 is mounted through an electromagnetic clutch $C_4$ to a lowermost horizontal link 31 of the supporting parallel linkage unit 30 so as to be rotatable about an axis $\alpha_3$ of rotation. One of two vertical links 32 of the supporting parallel linkage unit 30 on the near side of the operating microscope 33 is so curved as to retract from the operating microscope 33, thereby preventing interference with the operator. In this manner, the supporting parallel linkage unit 30 is cranked in shape as a whole, so that a center 33a of the operating microscope 33 supported by the supporting parallel linkage unit 30 is positioned just under the front link 27 (i.e., on the vertical axis $\alpha_2$). The operating microscope 33 is adapted to be moved for adjustment along the axes $\alpha_2$ and $\alpha_3$ and along an axis containing the center 33a and extending in a direction perpendicular to the plane of the sheet of FIGS. 5 and 6 by means of a sliding mechanism not shown. Accordingly, the center 33a can be set on the axes $\alpha_2$ and $\alpha_3$ by using this adjusting mechanism. The vertical links 32 of the supporting parallel linkage unit 30 are kept always parallel to the front link 27, and the horizontal link 31 only is changed in angle to thereby change an observation angle of the operating microscope 33. A vertically deformed condition of the supporting parallel linkage unit 30 can be locked by an electromagnetic clutch $C_5$.

An L-shaped crank member 34 is supported to the joint shaft $\beta_1$ at a rear or base end of of the supporting link 26. On the crank member 34 are set a horizontal fulcrum $\beta_6$ lying on a horizontal line $L_1$ on which the joint shaft $\beta_1$ lies and a vertical fulcrum $\beta_7$ lying on a vertical line $L_2$ on which the joint shaft $\beta_1$ lies. Further, a joint shaft $\beta_8$ is provided on the stand 18 at a position lying on a horizontal line $L_3$ on which the fulcrum 19 lies. The horizontal fulcrum $\beta_6$ and the joint shaft $\beta_8$ are connected together by a vertical sublink 37 parallel to the vertical link 21 and having the same length as that of a straight line extending between the fulcrum 19 and the joint shaft $\beta_1$. On the other hand, the vertical fulcrum $\beta_7$ on the crank member 34 and a joint shaft $\beta_9$ provided on the front link 27 at an upper end portion thereof are connected together by a horizontal sublink 38 parallel to the supporting link 26 and having the same length as that of the supporting link 26 (i.e., the length of a straight line extending between the joint shaft $\beta_1$ and the joint shaft $\beta_5$). Accordingly, in view of a mechanism, the fulcrum 19, the joint shaft $\beta_1$, the joint shaft $\beta_6$, and the joint shaft $\beta_8$ form a "parallel linkage", whereas the vertical fulcrum $\beta_1$, the joint shaft $\beta_5$, the joint shaft $\beta_9$, and the joint shaft $\beta_7$ form another "parallel linkage".

Figure 7:
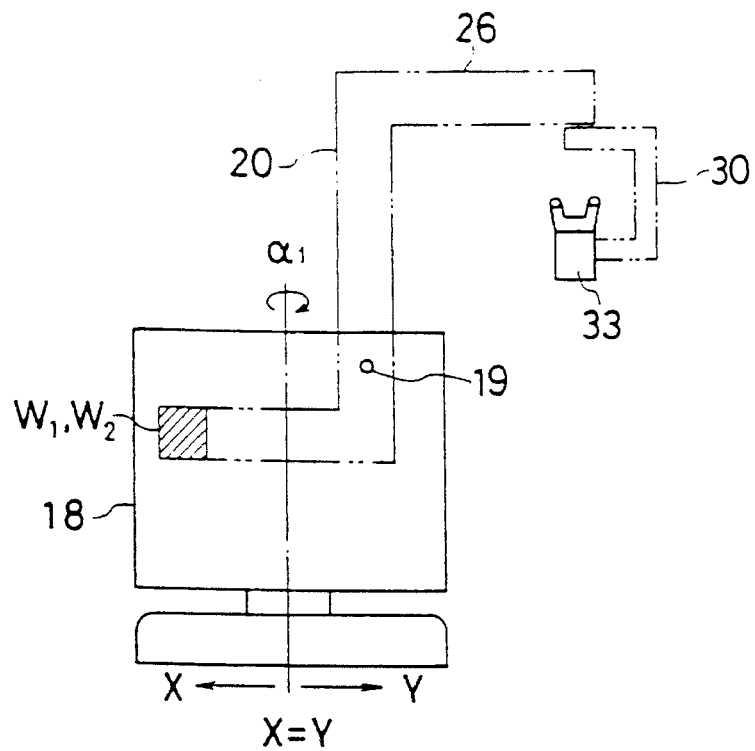
FIG. 7 is a schematic view illustrating a balancing structure with respect to a vertical axis of rotation as viewed in side elevation of the stand apparatus.
Figure 8:
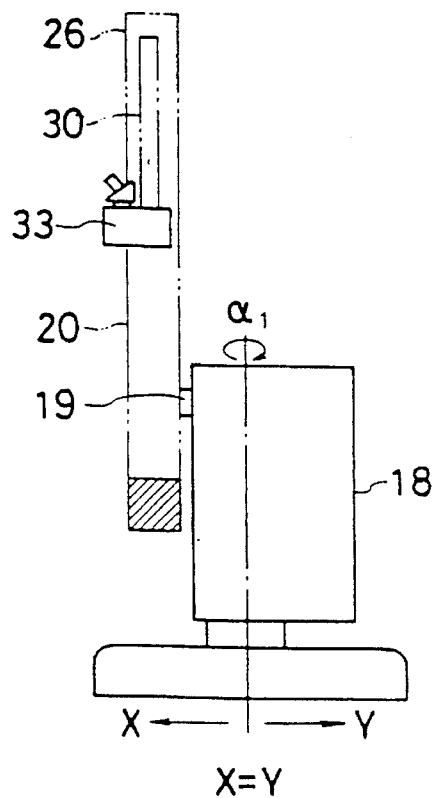
FIG. 8 is a schematic view illustrating a balancing structure with respect to the vertical axis of rotation as viewed in front elevation of the stand apparatus.

The stand apparatus according to this preferred embodiment has not only the above-mentioned mechanical feature but also the following feature in view of weight balance. That is, as shown in FIGS. 7 and 8, the stand apparatus as a whole is designed and adjusted so that a right-hand weight Y and a left-hand weight Y with respect to the vertical axis $\alpha_1$ are equalized as viewed both in a side elevation (FIG. 7) and in a front elevation (FIG. 8). Thus, the weight balance of the stand apparatus as a whole is ensured with respect to the vertical axis $\alpha_1$ in each of two perpendicular directions. Accordingly, even when the electromagnetic clutch $C_1$ is disengaged in a condition where the stand apparatus is set on the floor F that is inclined, there is no possibility that the stand 18 and the structure thereabove may spontaneously rotate about the vertical axis $\alpha_1$. This is due to the same mechanical function as that in assuming a "cylinder" freely rotatable about the vertical axis $\alpha_1$ wherein even when the "cylinder" is set on an inclined surface, the "cylinder" does not spontaneously rotate. Accordingly, after moving the stand apparatus from one place to another, it is unnecessary to carry out any troublesome horizontal adjustment of the stand apparatus at the new place.

The mechanical operation of the stand apparatus mentioned above will now be described.

Figure 2:
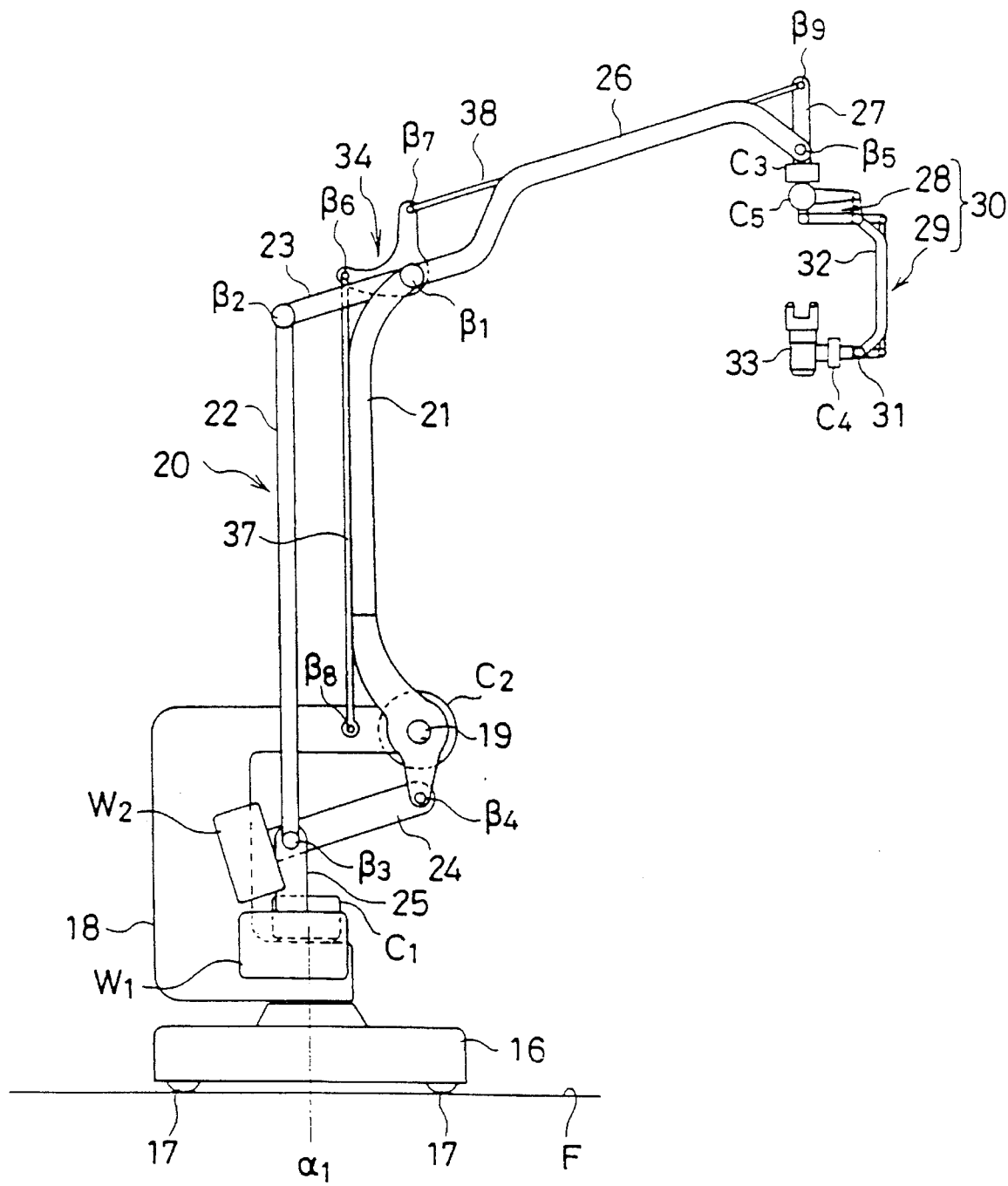
FIG. 2 is a side view similar to FIG. 1, showing a condition where the medical optical equipment is raised.
Figure 3:
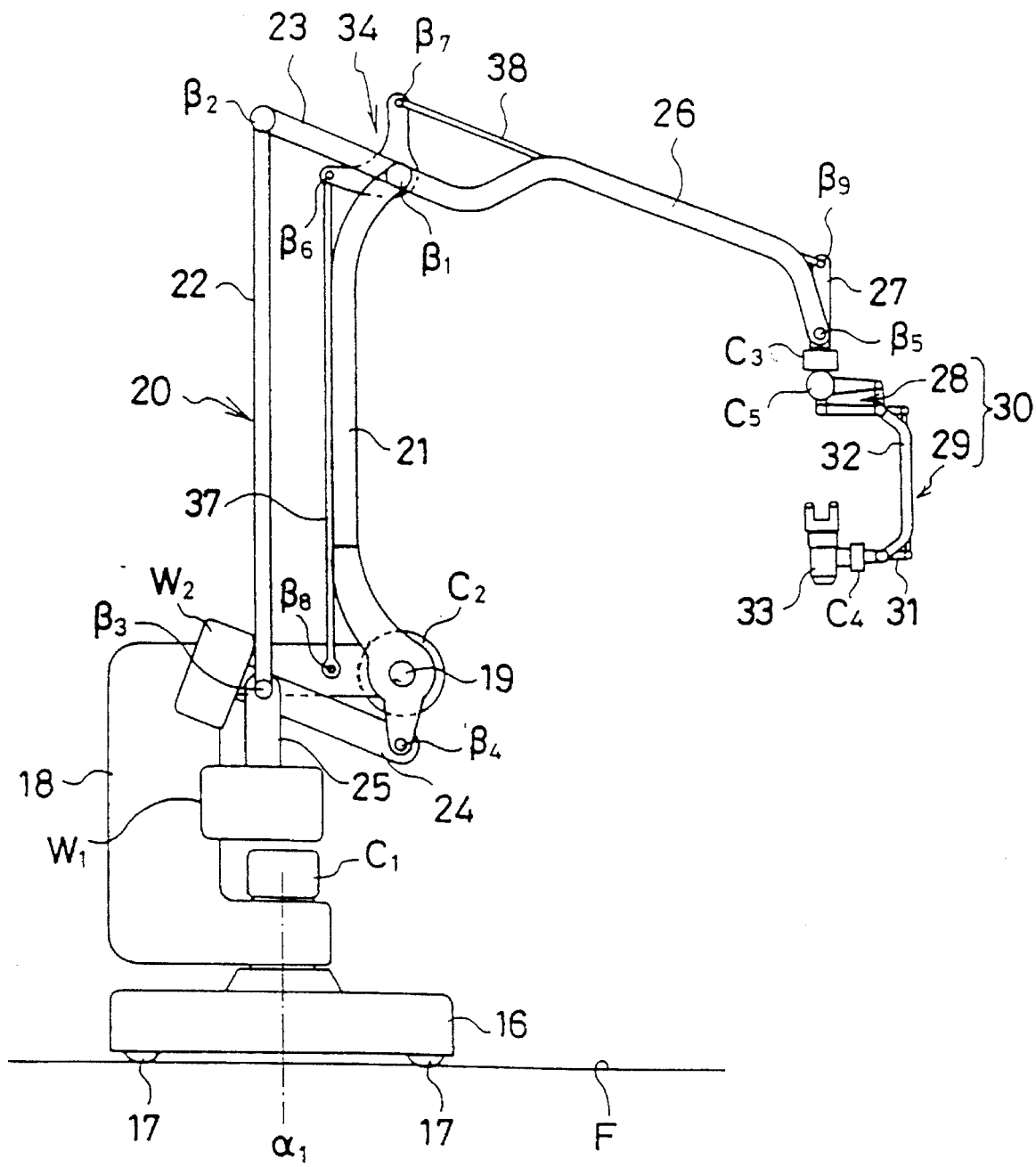
FIG. 3 is a side view similar to FIG. 1, showing a condition where the medical optical equipment is lowered.
Figure 4:
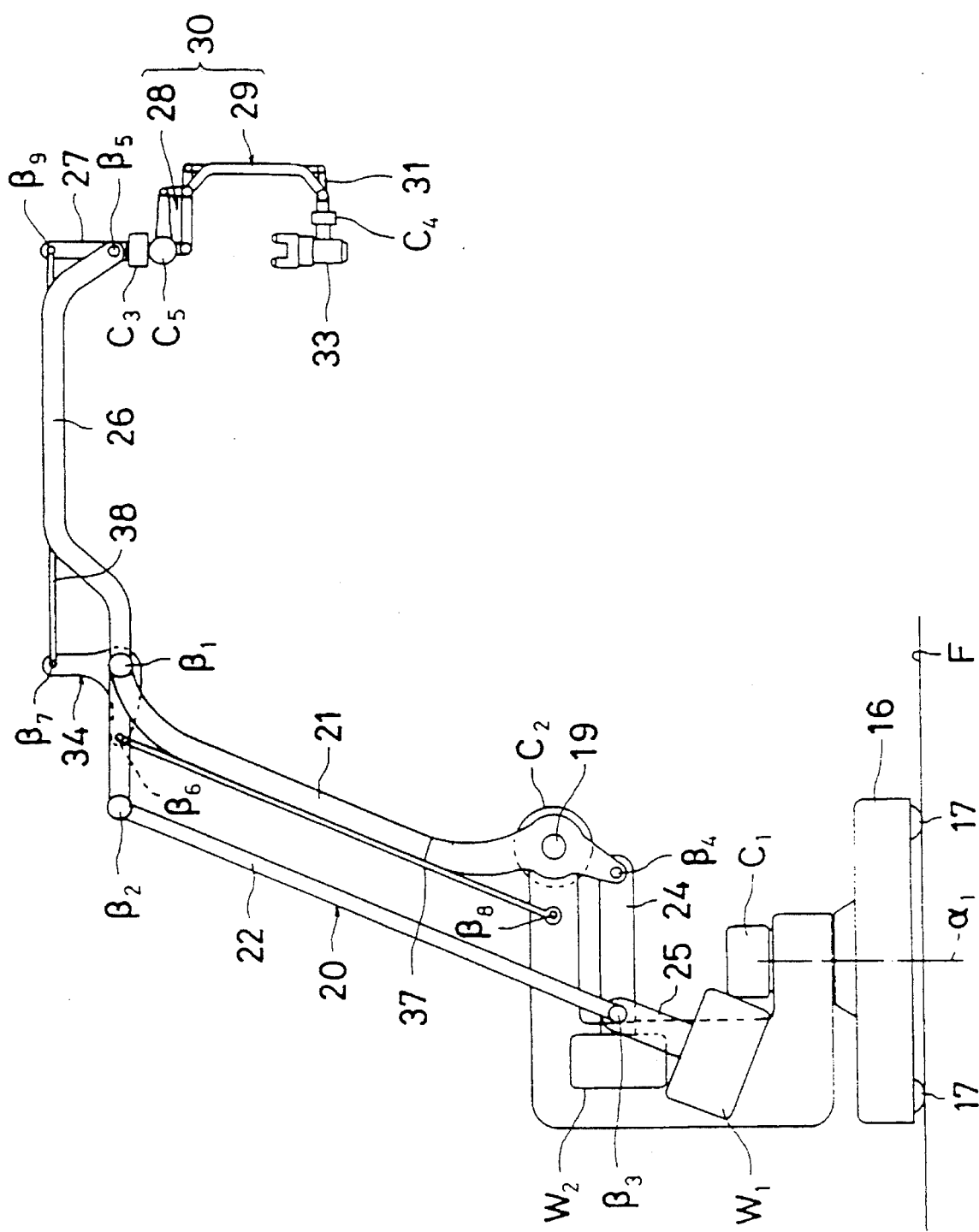
FIG. 4 is a side view similar to FIG. 1, showing a condition where the medical optical equipment is horizontally moved away from a stand.

The most characteristic point in the mechanical operation of the stand apparatus is that the crank member 34 does not rotate. That is, the horizontal fulcrum $\beta_6$ always lies on the horizontal line $L_1$ passing the joint shaft $\beta_1$, and the vertical fulcrum $\beta_7$ always lies on the vertical line $L_2$ passing the joint shaft $\beta_1$. Accordingly, when the supporting link 26 is raised or lowered to thereby raise or lower the operating microscope 33 as shown in FIG. 2 or 3, the joint shaft $\beta_1$ and the vertical fulcrum $\beta_7$ remains still, so that the front link 27 as the link opposite to a parallel link formed between the joint shaft $\beta_1$ and the vertical fulcrum $\beta_7$ in the parallel linkage is kept always in the vertical condition.

Further, when the main parallel linkage 20 is rotated about the fulcrum 19 to thereby move the operating microscope 33 in a frontward direction (FIG. 4) or in a rearward direction, the crank member 34 remains still, so that the front link 27 is kept always in the vertical direction. In this manner, the front link 27 is kept always in the vertical condition regardless of vertical and horizontal movements of the operating microscope 33. Therefore, there is no possibility that the front link 27 may interfere with the operator or the like during operation of the stand apparatus.

In changing the observation angle of the operating microscope 33, the supporting parallel linkage unit 30 supported under the front link 27 is rotated about the vertical axis $\alpha_2$ or is deformed to thereby set a desired angle. Also in this case, the vertical links 32 of the supporting parallel linkage unit 30 are kept always in the vertical condition, thereby preventing interference with the operator or the like.

Additionally, in raising or lowering the supporting link 26 (FIG. 2 or 3) or in horizontally moving the supporting link 26 away from the stand 18 (FIG. 4), the total weight of the parts supported at the fulcrum 19 inclusive of the parallel linkage 20, the supporting link 26, the supporting parallel linkage unit 30, and the operating microscope 33, are counterbalanced by the first counterweight $W_1$ and the second counterweight $W_2$. Accordingly, even when the electromagnetic clutch $C_2$ is disengaged to permit the operating microscope 33 to be moved by the hand of the operator or the like, and the operating microscope 33 is freed from the hand at any position after moved, the operating microscope 33 is kept stopped at this position. Particularly in horizontally moving the operating microscope 33 away from the stand 18 (FIG. 4), the first counterweight $W_1$ is moved opposite to the operating microscope 33 by the lever 25 pivoted integrally with the vertical link 22, thereby effecting reliable weight balance.

Figure 9:
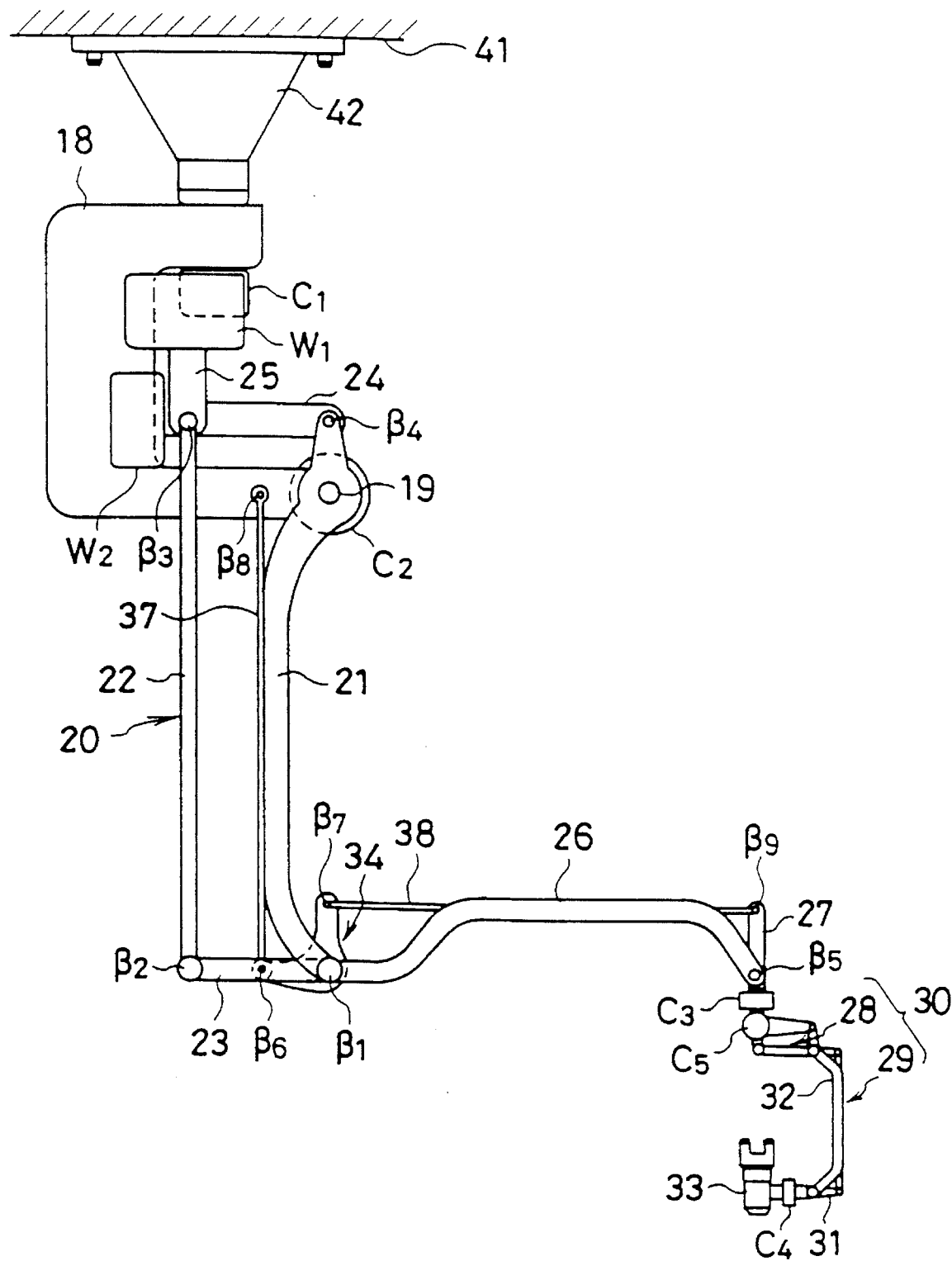
FIG. 9 is a side view of a stand apparatus for a medical optical equipment according to a second preferred embodiment of the present invention.
Figure 10:
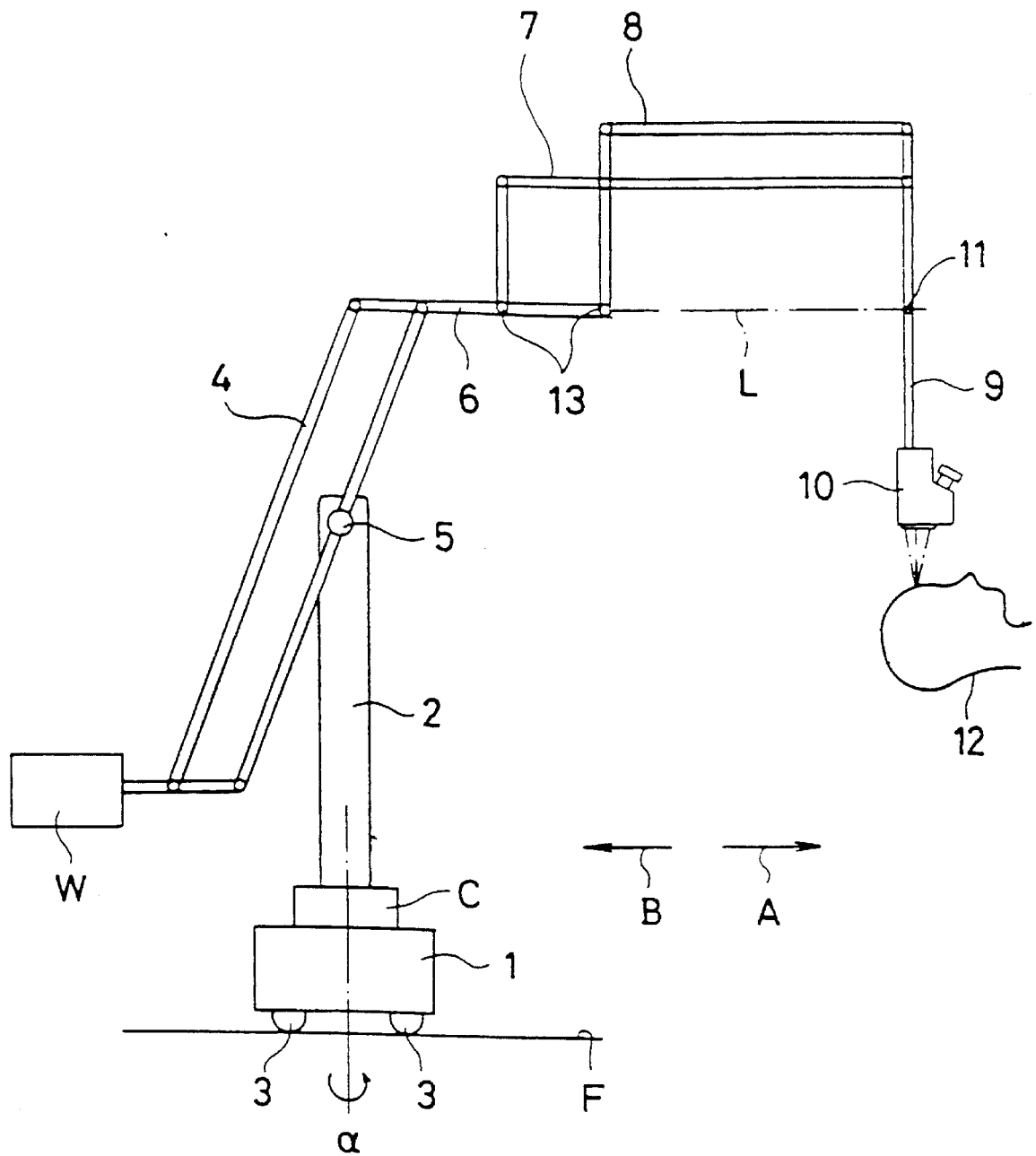
FIG. 10 is a side view of a stand apparatus for a medical optical equipment in the prior art.
Figure 11:
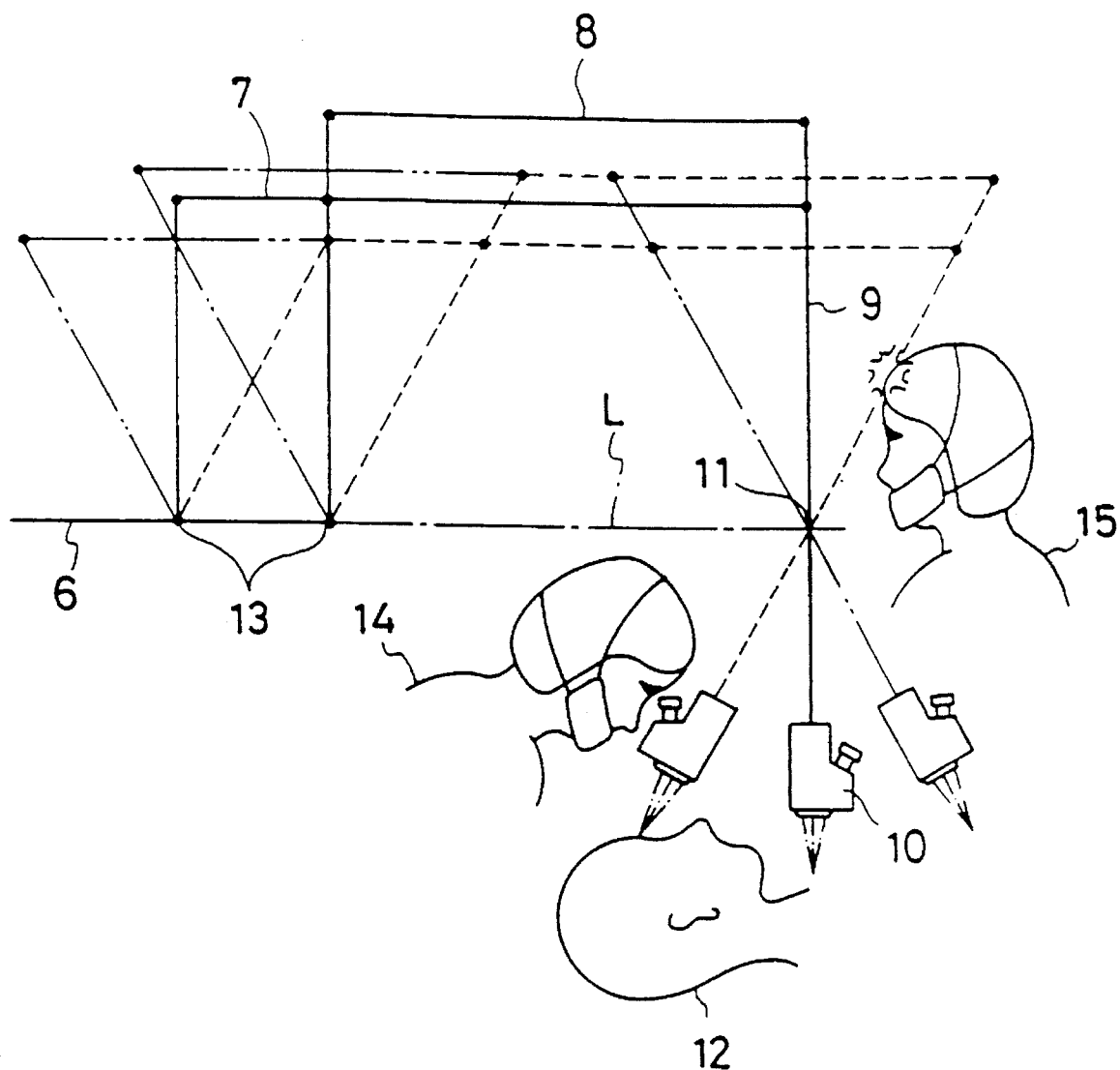
FIG. 11 is a schematic view illustrating a deformed condition of a parallel linkage of the stand apparatus shown in FIG. 10.

FIG. 9 shows a second preferred embodiment of the present invention. While the first preferred embodiment mentioned above is a floor disposition type of stand apparatus, the second preferred embodiment is a ceiling disposition type of stand apparatus. That is, the stand 18 and the structure therebelow in the second preferred embodiment are vertically inverted from the structure of the first preferred embodiment. A base 42 is fixed to a ceiling 41, and the stand 18 is mounted on a lower surface of the base 42 so as to be rotatable about the vertical axis $\alpha_1$. The other structure is similar to that of the first preferred embodiment, so that the same parts as those of the first preferred embodiment are denoted by the same reference numerals and the double explanation thereof will be omitted. Also in this type where the stand apparatus is set on the ceiling 41, the weight balance in each of at least two perpendicular directions with respect to the vertical axis $\alpha_1$ is provided. Accordingly, even when the vertical axis $\alpha_1$ is slightly inclined during long-term use of the stand apparatus, there is no inconvenience that the stand 18 and the structure therebelow may spontaneously rotate at the instance the electromagnetic clutch $C_1$ is disengaged.

Having thus described the floor disposition type of stand apparatus and the ceiling disposition type of stand apparatus, the present invention may be applied to a wall disposition type of stand apparatus in which the stand 18 is disposed on a wall of an operating room.

As described above, in the stand apparatus for the medical optical equipment according to the present invention, even when the main parallel linkage is deformed to move the medical optical equipment in the vertical direction and/or the horizontal direction, the front link supporting the medical optical equipment is kept always in the substantially vertical condition. Accordingly, there is no danger that the front link may largely swing to strike against any persons near the stand apparatus. Thus, the stand apparatus of the present invention is desirable from the viewpoints of operability and sanitariness.

Furthermore, the weight balance of the stand and the structure thereabove in each of at least two perpendicular directions with respect to a vertical axis of rotation of the stand is provided. Accordingly, even when the stand is disposed on an inclined floor, the stand and the structure thereabove do not spontaneously rotate. As a result, it is unnecessary to carry out horizontal adjustment of the stand apparatus after moving the stand apparatus from one place to another, thereby greatly simplifying the handling of the stand apparatus.

Industrial Applicability

As described above, in the stand apparatus for the medical optical equipment according to the present invention, even when the main parallel linkage is deformed to move the medical optical equipment in the vertical direction and/or the horizontal direction, the front link supporting the medical optical equipment is always kept in the substantially vertical condition. Accordingly, there is no possibility that the front link may largely swing to strike against any persons near the stand apparatus. Thus, the stand apparatus of the present invention is desirable for retention of the medical optical equipment that is required to ensure high operability and sanitary control in an operating room.

I claim:

1. A stand apparatus for medical optical equipment, comprising:

a pair of parallel vertical links and a pair of parallel horizontal links combined to form a parallel linkage, and an intermediate portion of a first one of said vertical links being pivotally supported through a first fulcrum to a stand;

an upper one of said horizontal links of said parallel linkage being extended to form a supporting link, and a substantially vertical front link being pivotally supported to said supporting link at a front end of said supporting link, said medical optical equipment being supported to a lower end of said vertical front link;

a joint shaft of said parallel linkage being set at a rear end of said supporting link, and a crank member supported by said joint shaft, said crank member having a horizontal fulcrum lying on a horizontal line on which said joint shaft lies and a vertical fulcrum lying on a vertical line on which said joint shaft lies, said horizontal fulcrum of said crank member and a portion of said stand being connected together by a vertical sublink parallel to said first one of said vertical links of said parallel linkage and having a length equal to the linear distance between said joint shaft of said first one of said vertical links and said first fulcrum of said parallel linkage, said vertical fulcrum of said crank member and a portion of said front link being connected together by a horizontal sublink parallel to said supporting link and having a length equal to that of said supporting link; and a counterweight provided below said parallel linkage to counterbalance a weight applied in a lowering direction of said parallel linkage about said first fulcrum and thereby keep said medical optical equipment stationary in a floating condition.

2. A stand apparatus for medical optical equipment according to claim 1, wherein a supporting parallel linkage unit having vertical links is provided at a lower end of said front link, and said medical optical equipment is supported to a lowermost horizontal link of said supporting parallel linkage unit.

3. A stand apparatus for medical optical equipment according to one of claims 1 or 2, wherein said stand is rotatably mounted on a base disposed on said floor so as to be rotatable about a substantially vertical axis of rotation, and a weight of said stand and a portion of said stand apparatus above said stand is balanced with respect to said substantially vertical axis in each of at least two perpendicular directions.

4. A stand apparatus for medical optical equipment according to one of claims 1 or 2, wherein said stand is disposed on a wall of a room.

5. A stand apparatus for medical optical equipment, comprising:

a pair of parallel vertical links and a pair of parallel horizontal links combined to form a parallel linkage, an intermediate portion of a first one of said vertical links of said parallel linkage being pivotally supported through a first fulcrum to a stand disposed on a ceiling;

a lower end of said horizontal links of said parallel linkage being extended to form a supporting link, and a substantially vertical front link being pivotally supported to said supporting link at a front end of said supporting link, said medical optical equipment being supported to a lower end of said vertical front link;

a joint shaft of said parallel linkage being set at a rear end of said supporting link, and a crank member supported by said joint shaft, said crank member having a horizontal fulcrum lying on a horizontal line on which said joint shaft lies and a vertical fulcrum lying on a vertical line on which said joint shaft lies, said horizontal fulcrum of said crank member and a portion of said stand being connected together by a vertical sublink parallel to said first one of said vertical links of said parallel linkage and having a length equal to the linear distance between said joint shaft of said first one of said vertical links and said first fulcrum of said parallel linkage, said vertical fulcrum of said crank member and a portion of said front link being connected together by a horizontal sublink parallel to said supporting link and having a length equal to that of said supporting link; and a counterweight provided above said parallel linkage to counterbalance a weight applied in a lowering direction of said parallel linkage about said first fulcrum and thereby keep said medical optical equipment stationary in a floating condition.

6. A stand apparatus for medical optical equipment according to claim 1, wherein said stand is disposed on a floor.

* * * * *